United States Patent
Wang et al.

(10) Patent No.: US 10,420,529 B2
(45) Date of Patent: Sep. 24, 2019

(54) ARRHYTHMIA DETECTION DEVICE

(71) Applicant: SHENZHEN MINDRAY BIO-MEDICAL ELECTRONICS CO., LTD., Shenzhen (CN)

(72) Inventors: Cheng Wang, Beijing (CN); Yong Li, Beijing (CN); Yi Han, Beijing (CN); Shuo Liu, Beijing (CN); Liang Chen, Beijing (CN); Yang Liu, Beijing (CN); Haibo Song, Beijing (CN); Jin Liu, Beijing (CN); Yunxia Zuo, Beijing (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 772 days.

(21) Appl. No.: 15/094,824

(22) Filed: Apr. 8, 2016

(65) Prior Publication Data

US 2016/0220225 A1     Aug. 4, 2016

Related U.S. Application Data

(63) Continuation-in-part of application No. PCT/CN2014/074282, filed on Mar. 28, 2014.

(30) Foreign Application Priority Data

Oct. 10, 2013 (CN) .......................... 2013 1 0469959

(51) Int. Cl.
*A61B 8/08* (2006.01)
*A61B 8/00* (2006.01)
(Continued)

(52) U.S. Cl.
CPC .......... *A61B 8/0883* (2013.01); *A61B 5/0464* (2013.01); *A61B 8/02* (2013.01);
(Continued)

(58) Field of Classification Search
CPC ....... A61B 5/0464; A61B 8/02; A61B 8/0883; A61B 8/42; A61B 8/4209; A61B 8/5223; A61B 8/543
See application file for complete search history.

(56) References Cited

U.S. PATENT DOCUMENTS

2005/0288585 A1   12/2005   Zamboglu et al.
2009/0247872 A1*  10/2009   Rowlandson ........ A61B 5/0402
                                                600/438

FOREIGN PATENT DOCUMENTS

CN   101500646 A   8/2009
CN   101543405 A   9/2009
(Continued)

*Primary Examiner* — Michael T Rozanski
(74) *Attorney, Agent, or Firm* — Kory D. Christensen

(57) ABSTRACT

An arrhythmia detection device is provided, which includes: a monitoring probe attached to a subject to be examined; a monitoring unit coupled with the monitoring probe; a first displaying unit which displays ECG parameters obtained by the monitoring unit; an ultrasound probe attached onto a body surface of the subject; an ultrasound imaging unit coupled with the ultrasound probe; an arrhythmia triggering unit which triggers the ultrasound imaging unit to scan the heart of the subject when the monitoring unit detects an arrhythmia; and a second displaying unit which displays the images and/or the parameters of the heart obtained by the ultrasound imaging unit.

16 Claims, 3 Drawing Sheets

(51) Int. Cl.
*A61B 8/02* (2006.01)
*A61B 5/0464* (2006.01)

(52) U.S. Cl.
CPC .............. *A61B 8/42* (2013.01); *A61B 8/5223* (2013.01); *A61B 8/543* (2013.01); *A61B 8/4209* (2013.01)

(56) References Cited

FOREIGN PATENT DOCUMENTS

CN 103126718 A 6/2013
JP 2002272740 A 9/2002

\* cited by examiner

ARRHYTHMIA DETECTION DEVICE

CROSS-REFERENCE TO RELATED APPLICATIONS

This application is a continuation-in-part of Patent Cooperation Treaty (PCT) Application No. PCT/CN2014/074282, filed Mar. 28, 2014, for "Arrhythmia Detection Device," which claims the benefit of Chinese Patent Application No. 201310469959.5, filed on Oct. 10, 2010, which is incorporated herein by reference.

TECHNICAL FIELD

The present disclosure generally relates to medical devices, in particular to arrhythmia detection devices.

BACKGROUND

Asystole is one kind of arrhythmia which has high seriousness level. Existing patient monitors will alert for the asystole in conditions that:
 1) the patient monitor has a function of asystole analysis;
 2) the ECG leads are correctly connected onto the subject to be examined;
 3) the asystole alarm switch is on;
 4) voltage of the ECG signal detected by the patient monitor is lower than an asystole threshold (low-voltage ECG signal); and
 5) duration of the low-voltage ECG signal exceeds a set threshold.

It can be seen from the conditions for asystole alarm mentioned above that any factor which can result in a low-voltage ECG signal with enough duration may result in an asystole alarm, which may lead to false alarms for asystole. Other reasons for false alarm for asystole may be:
 1) that the ECG leads are not connected well, which leads to too large resistance between the electrodes and the skin of the subject to be examined;
 2) that the ECG leads are connected to the subject to be examined at incorrect positions, which leads to too weak ECG signals;
 3) electromagnetic interference from the surroundings, which leads to too weak ECG signals; or
 4) other reasons which may result in false alarm for asystole.

Therefore, detection errors may occur during asystole detection by an existing patient monitor, thereby a false alarm may be generated. Furthermore, other arrhythmias, such as ventricular tachycardia (VT), ventricular fibrillation (VF) or the like, may also result in false alarm.

SUMMARY

In some embodiments, an arrhythmia detection device is provided, which can trigger an ultrasound imaging unit to scan a heart of a patient when a monitoring unit detects arrhythmia. The arrhythmia detection device may include: a monitoring probe which is attached to a subject to be examined; a monitoring unit which is coupled with the monitoring probe and obtains ECG parameters of the subject using the monitoring probe; a first displaying unit which displays the ECG parameters obtained by the monitoring unit; an ultrasound probe which is attached onto a body surface of the subject; an ultrasound imaging unit which is coupled with the ultrasound probe; an arrhythmia triggering unit which triggers the ultrasound imaging unit to control the ultrasound probe to transmit ultrasound waves towards a heart of the subject to scan the heart, receive ultrasound echo signals and obtain images and/or parameters of the heart based on the ultrasound echo signals when the monitoring unit detects an arrhythmia; and a second displaying unit which displays the images and/or the parameters of the heart obtained by the ultrasound imaging unit.

BRIEF DESCRIPTION OF THE DRAWINGS

In order to describe the technical solutions in embodiments of the present disclosure or in the art more clearly, the drawings to be cited in the description now will be described briefly. However, it is obvious that the drawings described thereafter are merely some embodiments of the present disclosure and other drawings may be obtained by a person ordinary skilled in the art based on these drawings without creative work.

DETAILED DESCRIPTION

Specific details are provided thereafter for complete understanding of the embodiments and for implementation of the embodiments by a person skilled in the art. However, the person skilled in the art will understand that the embodiments can also be implemented without these details. In some embodiments, well known structures and functions are not shown or described in details in order to avoid unnecessary confusion of the description of the embodiments.

Unless described expressly, the terms "include", "comprise" and the like throughout the description and the claims should be interpreted as inclusive, but not exclusive or exhaustive. In other words, their meanings are "including but not limited to".

In some embodiments, arrhythmia detection devices are provided, which may trigger an ultrasound imaging for a heart of a subject under examination when an arrhythmia (such as asystole, VT or VF, etc.) is detected by a monitoring unit. By the ultrasound imaging, mechanical activities of the heart can be presented and motion state of the heart can be visually shown. In order to address the issue of false alarm for arrhythmia (for example, asystole, VT or VF, etc), the data or signals obtained by the ultrasound imaging may be used to verify the results of ECG monitoring of the monitoring unit. Therefore, the false alarm may be reduced.

Figure 1:
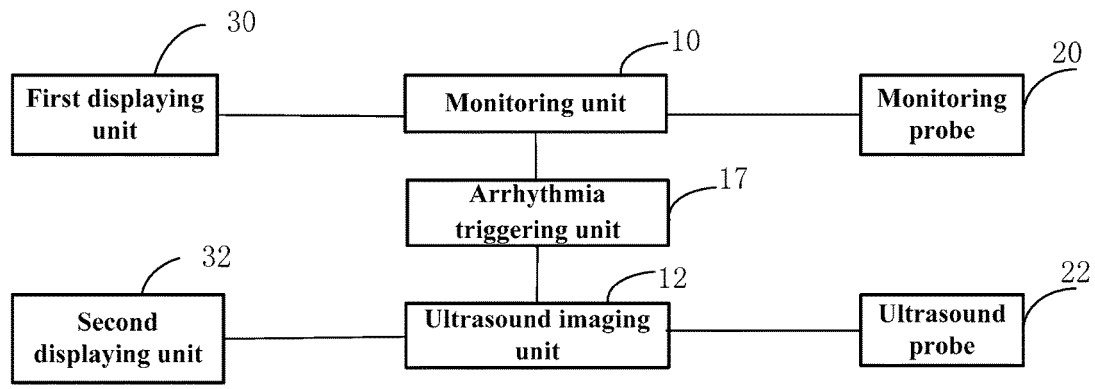
FIG. 1 is a schematic view of an arrhythmia detection device according to an embodiment.

Referring to FIG. 1, an arrhythmia detection device is provided. The arrhythmia detection device may include an ultrasound probe 22 which may be attached onto a body surface of the subject to be examined and may transmit ultrasound waves towards the subject to scan the heart of the subject. Specifically, the ultrasound probe 22 may be tightly attached onto the body surface of the subject to be examined at determined locations and scan a section of the subject at the determined locations. Furthermore, the angle of the ultrasound probes 22 may be freely adjusted in order to obtain ultrasound echo signals at different locations. The ultrasound probe 22 may be attached onto the body surface in a variety of ways and therefore a real-time, continuous ultrasound echo signals of the heart of the subject may be obtained without the requirement of hand-holding the ultrasound probe.

The arrhythmia detection device may further include a monitoring probe 20 which may be attached to the subject under examination and may detect ECG parameters of the subject.

The arrhythmia detection device may further include an ultrasound imaging unit 12. The ultrasound imaging unit 12 may be coupled to the ultrasound probe 22 and may control the ultrasound probe 22 to transmit ultrasound waves towards the subject and receive ultrasound echo signals obtained by the ultrasound probe 22. Images of the heart may be obtained based on the ultrasound echo signals, and thereby physiological parameters of the heart, such as ejection fraction, left ventricular fractional shortening, stroke volume, cardiac output, cardiac index, left ventricular end-diastolic volume, left ventricular end-systolic volume, or the like, may be obtained based on the ultrasound echo signals and/or the images of the heart. Based on the physiological parameters and/or the images, other parameters of the heart may be calculated, such as total number of times of ventricular rhythm abnormalities during a period of time (for example, which may be set as 24 hours, or be same as the duration of ECG signal collection, etc.), dynamic area-time curve of left ventricle, tendency chart (curved surface) of area-time curves and variability thereof, dynamic M mode motion curve of left ventricle, dynamic ascend velocity, dynamic descend velocity, ascend time, descend time and/or amplitude of each heartbeat, tendency chart and variability thereof, identification and/or alarm for nonsustained ventricular tachycardia or ventricular fibrillation, average end-diastolic volume, average end-systolic volume, average stroke volume, average ejection fraction, average fractional shortening, or the like.

The arrhythmia detection device may further include a monitoring unit 10. The monitoring unit 10 may be coupled to, and obtain ECG parameters of the subject under examination through, the monitoring probe 20. The ECG parameters may include average heart rate during a period of time (for example, 24 hours, etc.), QT interval, PR interval, RR interval, total number of sinus rhythm, number of premature ventricular contraction (PVC), percentage of PVC in sinus rhythm, width of QRS wave of PVC, classification and counting of arrhythmia events, or the like.

The arrhythmia detection device may further include a first displaying unit 30 which may display the ECG parameters obtained by the monitoring unit 10, and a second displaying unit 32 which may display the information of the heart (for example, the images and/or parameters of the heart) obtained by the ultrasound imaging unit 12.

The arrhythmia detection device may further include an arrhythmia triggering unit 17 which may trigger the ultrasound imaging unit 12 to scan the heart of the subject under examination through the ultrasound probe 22 as described above when the monitoring unit 10 detects an arrhythmia. In this case, the second displaying unit 32 may display information of the heart obtained by the ultrasound imaging unit 12 at the time of the arrhythmia. For example, in some embodiments, the second displaying unit 32 may display the images and/or the parameters (such as the physiological parameters and/or other parameters calculated based on the images and/or the physiological parameters) of the heart obtained by the ultrasound imaging unit 12 at the time of the arrhythmia. The first displaying unit 30 may display the ECG parameters obtained by the monitoring unit 10 at the time of the arrhythmia. The "ECG parameters" herein may refer to conventional ECG parameters, for example, common ECG parameters obtained by conventional/common monitoring equipments (for example, patient monitor or ECG machine). The first displaying unit 30 may be a displaying unit which displays conventional monitoring information. The conventional monitoring information herein may be general monitoring information obtained by conventional/common monitoring equipment, including common ECG information, respiration information, blood oxygen information, etc.

Figure 2:
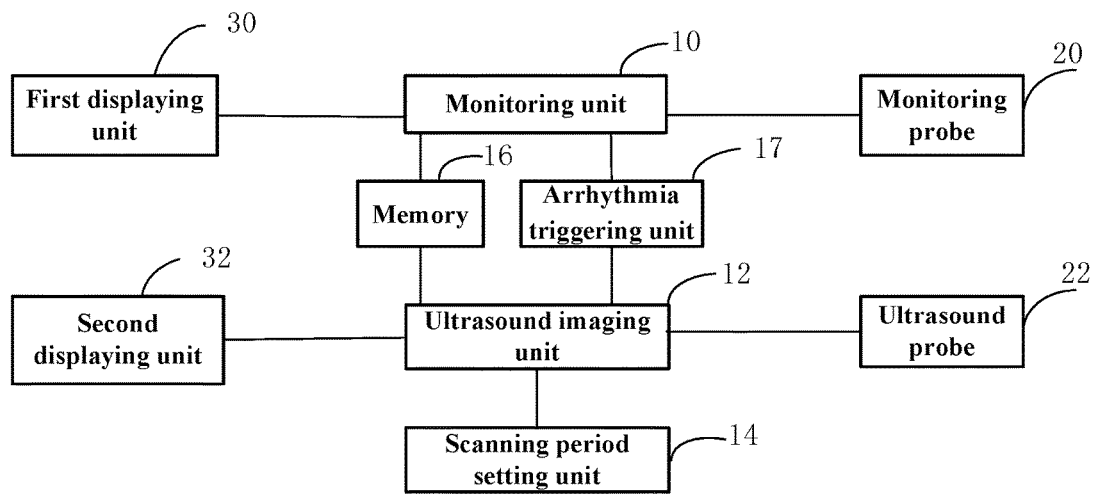
FIG. 2 is a schematic view of an arrhythmia detection device according to another embodiment.

Referring to FIG. 2, in another embodiment, the arrhythmia detection device may further include a memory 16 and a scanning period setting unit 14. The memory 16 may store the images and/or the parameters (for example, the physiological parameters and/or other parameters) obtained by the ultrasound imaging unit 12 and/or the ECG parameters obtained by the monitoring unit 10. The scanning period setting unit 14 may set the time interval of the ultrasound scanning performed by the ultrasound imaging unit 12.

In some embodiments, the ultrasound imaging unit 12 and the monitoring unit 10 may be separate from each other. In some embodiments, the ultrasound imaging unit 12 and the monitoring unit 10 may be integrated into one host.

Figure 3:
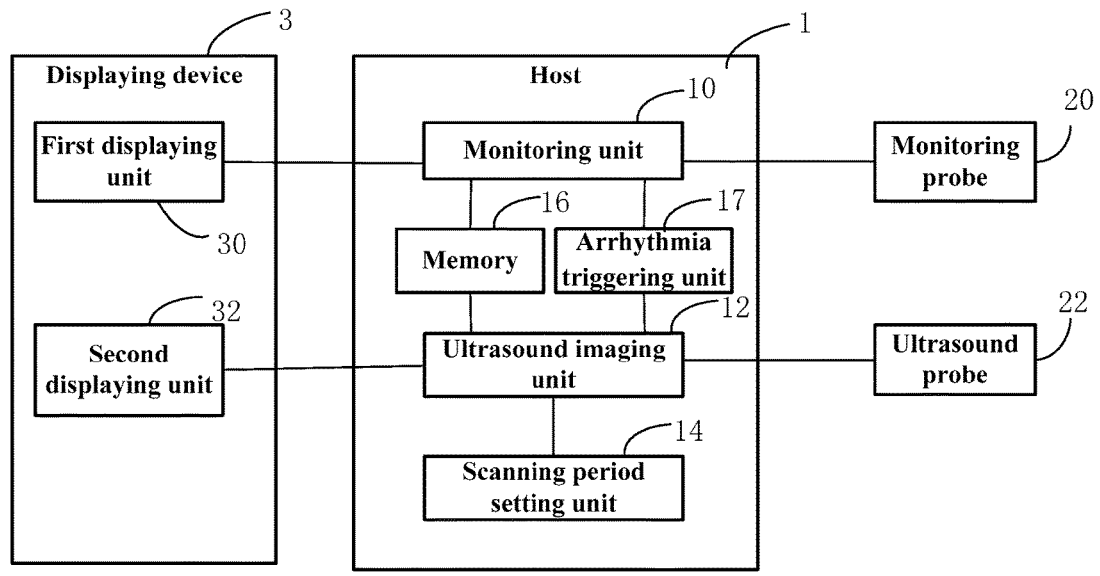
FIG. 3 is a schematic view of an arrhythmia detection device according to another embodiment.

Referring to FIG. 3, in some embodiments, the ultrasound imaging unit 12 and the monitoring unit 10 of the arrhythmia detection device may be integrated into a host 1, and the first displaying unit 30 and the second displaying unit 32 may be integrated into a displaying device 3.

Figure 4:
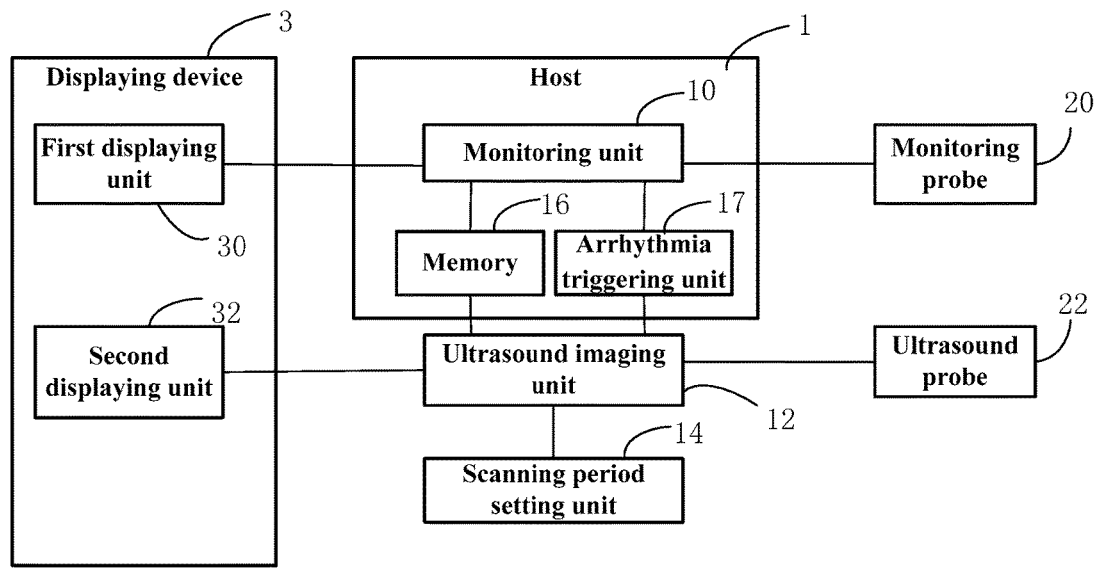
FIG. 4 is a schematic view of an arrhythmia detection device according to another embodiment.

Referring to FIG. 4, in some embodiments, the ultrasound imaging unit 12 and the monitoring unit 10 may be separate from each other. The monitoring unit 10 may be integrated into the host 1 and the ultrasound imaging unit 12 may be separate from the host 1.

Figure 5:
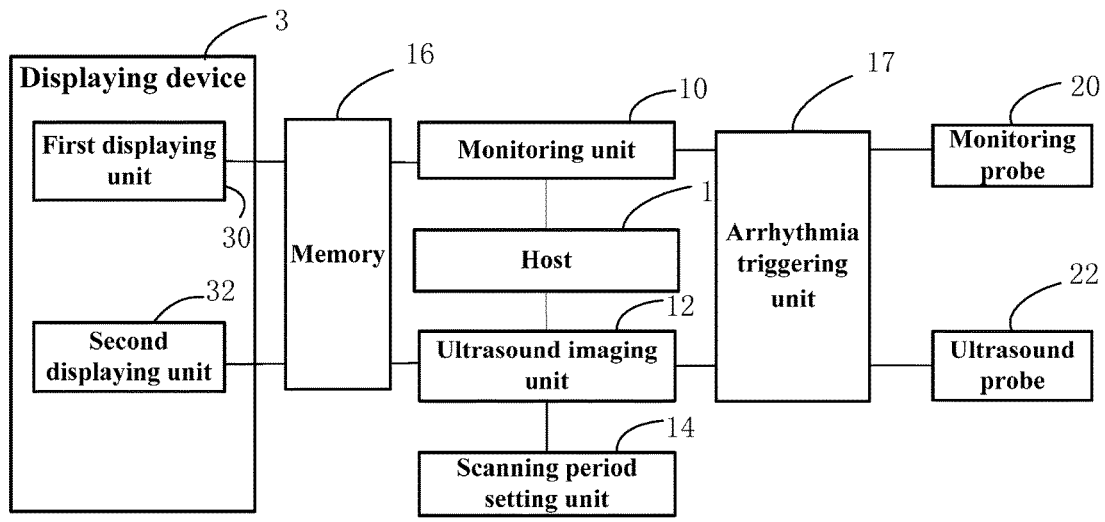
FIG. 5 is a schematic view of an arrhythmia detection device according to another embodiment.

In some embodiments, as shown in FIG. 2, the ultrasound imaging unit 12 may be directly connected with the monitoring unit 20. In some embodiments, as shown in FIG. 5, the ultrasound imaging unit 12 and the monitoring unit 10 may be detachable units which are separate from each other and are connected to the host 1 through interfaces arranged at the host 1.

Figure 6:
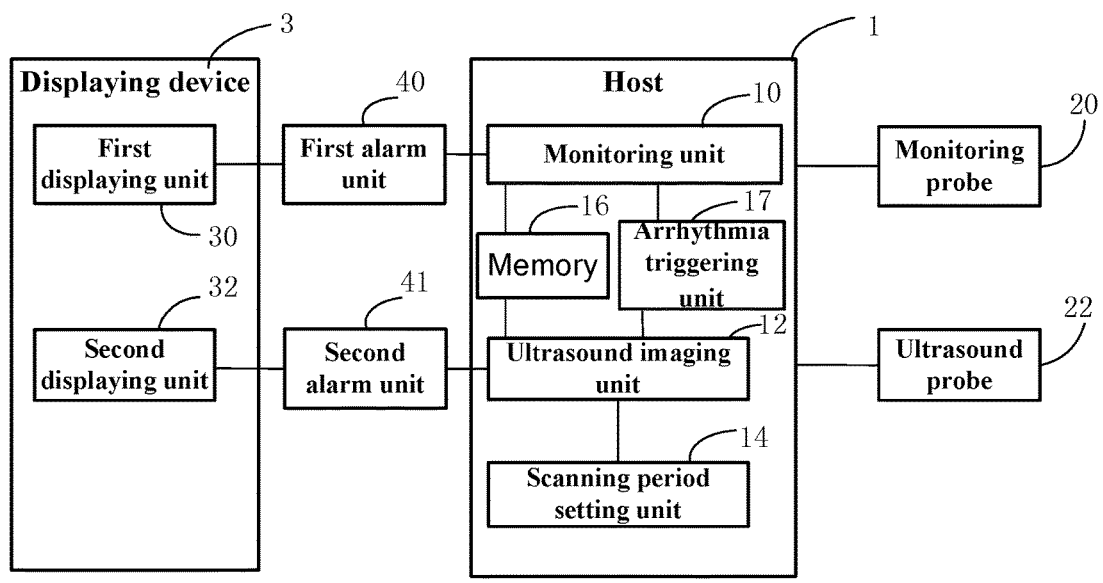
FIG. 6 is a schematic view of an arrhythmia detection device according to another embodiment.

Referring to FIG. 6, in some embodiments, the arrhythmia detection device may further include a first alarm unit 40. The first alarm unit 40 may output a first alarm when the monitoring unit 10 detects arrhythmia to inform that the monitoring unit 10 has detected an arrhythmia. The arrhythmia detected by the monitoring unit 10 may include asystole, ventricular tachycardia, ventricular fibrillation, or the like. The first alarm may be any suitable forms, such as an audio, a video, a dialog box, a highlighted portion on the display, a flashing portion on the display, text(s), flashing text(s), highlighted text(s), a portion color-coded with special color(s) and/or any other suitable forms.

The arrhythmia detection device may further include a second alarm unit 41 which may output a second alarm or a third alarm based on the images and/or the parameters (for example, the physiological parameters and/or other parameters) obtained by the ultrasound imaging unit 12.

For example, in some embodiments, when the images and/or the parameters of the heart obtained by the ultrasound imaging unit 12 satisfy the conditions of arrhythmia (for example, asystole, ventricular tachycardia and/or ventricular fibrillation, etc.), a second alarm may be output by the second alarm unit 41 to inform that the ultrasound imaging unit 12 has verified the occurrence of the arrhythmia. The second alarm herein may be any forms. For example, in some embodiments, the second alarm may be an audio, a video, a dialog box, a highlighted portion on the display, a flashing portion on the display, text(s), flashing text(s), highlighted text(s), a portion color-coded with special color(s) and/or any other suitable forms. In embodiments in which the first alarm unit 40 is omitted, the second alarm may be output in any suitable form at any suitable location. In embodiments in which the first alarm unit 40 presents, the second alarm may be output at different locations (for example, different positions on the display) from the first alarm, in this case the second alarm may be the same as or different from the first alarm; or, the second alarm may be output at the same location as the first alarm, in this case the second alarm may be different from the first alarm.

In some embodiments, when the images and/or the parameters of the heart obtained by the ultrasound imaging unit 12 do not satisfy the conditions of arrhythmia, a third alarm may be output by the second alarm unit 41 to inform that the ultrasound imaging unit 12 does not detect arrhythmia. The third alarm may be an audio, a video, a dialog box, a highlighted portion on the display, a flashing portion on the display, text(s), flashing text(s), highlighted text(s), a portion color-coded with special color(s) and/or any other suitable forms. In some embodiments, the third alarm may be different from the second alarm.

In some embodiments, there may be not third alarm. I.e., when the images and/or the parameters of the heart obtained by the ultrasound imaging unit 12 do not satisfy the conditions of arrhythmia, the second alarm unit 41 does not output an alarm.

For example, in some embodiments, when the images and/or the parameters of the heart obtained by the ultrasound imaging unit 12 satisfy the conditions of arrhythmia (for example, asystole, ventricular tachycardia and/or ventricular fibrillation, etc.), a highlight (which is the second alarm in these embodiment) may be displayed with a color differing from the color of the first alarm output by the alarm unit 40. Or, in some embodiments, the parameters and/or the images obtained by the ultrasound imaging unit 12 and/or at least a part of the user interface of the arrhythmia detection device may flash (which is the second alarm in these embodiment).

In some embodiments, when the images and/or the parameters of the heart obtained by the ultrasound imaging unit 12 do not satisfy the conditions of arrhythmia, the parameters and/or images obtained by the ultrasound imaging unit 12 and/or at least a part of the user interface of the arrhythmia detection device may flash (which is the third alarm in these embodiment).

Although the first alarm unit 40 and the second alarm unit 41 are described separately, they should not be limited thereto. It will be understood by a person skilled in the art that all of at least a part of the first and second alarm unit can be implemented in one unit.

The arrhythmia detection devices of the embodiments of the present disclosure can trigger the ultrasound imaging unit to scan the heart of the patient when the monitoring unit detect arrhythmia, such as asystole, ventricular tachycardia or ventricular fibrillation, etc. The state of asystole, ventricular tachycardia or ventricular fibrillation of the heart can be further verified through the images and/or parameters obtained by the ultrasound imaging unit and therefore the arrhythmia can be monitored more accurately.

The present disclosure has been described with reference to specific embodiments above. However, the embodiments of the present disclosure are not limited thereto. Other modifications and alternations can be made by a person ordinary skilled in the art without departing from the concept of the present disclosure, all of which should be within the scope of protection of the present disclosure.

What is claimed is:

1. An arrhythmia detection device, comprising:
   a monitoring probe configured to be attached to a subject to be examined;
   monitoring equipment which is coupled with the monitoring probe and obtains ECG parameters of the subject using the monitoring probe;
   and
   an ultrasound probe configured to be attached onto a body surface of the subject and provide, without being held by a hand, real-time ultrasound echo signals of a heart of the subject;
   an ultrasound imaging unit which is coupled with the ultrasound probe;
   wherein, when the monitoring equipment detects an arrhythmia, the ultrasound imaging unit is configured to control the ultrasound probe to transmit ultrasound waves towards the heart of the subject to scan the heart, receive the ultrasound echo signals, and obtain at least one of images and parameters of the heart based on the ultrasound echo signals;
   wherein a second alarm is generated when at least one of the images and parameters of the heart obtained by the ultrasound imaging unit satisfy conditions of arrhythmia to confirm the occurrence of the arrhythmia detected by the monitoring equipment; and
   wherein a third alarm is generated when both the images and the parameters of the heart obtained by the ultrasound imaging unit do not satisfy the conditions of arrhythmia to indicate that the occurrence of the arrhythmia detected by the monitoring equipment is false.

2. The arrhythmia detection device of claim 1, further comprising:
   a memory which stores at least one of the at least one of the images and the parameters of the heart obtained by the ultrasound imaging unit and the ECG parameters obtained by the monitoring equipment.

3. The arrhythmia detection device of claim 1, wherein a display displays the at least one of the images and parameters of the heart obtained by the ultrasound imaging unit.

4. The arrhythmia detection device of claim 1, wherein the ultrasound imaging unit and the monitoring equipment are integrated into a host.

5. The arrhythmia detection device of claim 1, wherein the ultrasound imaging unit and the monitoring equipment are separate from each other.

6. The arrhythmia detection device of claim 1, wherein the ultrasound imaging unit is directly connected with the monitoring equipment, or is connected with the monitoring equipment through a host.

7. The arrhythmia detection device of claim 1, wherein the ultrasound imaging unit and the monitoring equipment are detachable units which are separate from each other and are connected to a host through interfaces arranged at the host.

8. The arrhythmia detection device of claim 1, a wherein a first alarm is generated when the monitoring equipment detects the arrhythmia.

9. The arrhythmia detection device of claim 8, wherein the second alarm is different from the first alarm, or the second alarm is presented at a different position from the first alarm.

10. The arrhythmia detection device of claim 8, wherein the first alarm is at least one of an audio, a video, a highlighted portion on a display, and highlighted text.

11. The arrhythmia detection device of claim 8, wherein the first alarm is at least one of a flashing portion on a display, flashing text and a portion color-coded with special color or colors.

12. The arrhythmia detection device of claim 1, wherein the arrhythmia comprises at least one of asystole, ventricular tachycardia and ventricular fibrillation.

13. The arrhythmia detection device of claim 1, wherein the third alarm is different from the second alarm.

14. The arrhythmia detection device of claim 1, wherein at least one of the second alarm and third alarm is at least one of an audio and a video.

15. The arrhythmia detection device of claim 1, wherein at least one of the second alarm and third alarm is at least one of a highlighted portion on a display, a flashing portion on the display, a flashing text, and highlighted text.

16. The arrhythmia detection device of claim 1, wherein at least one of the second alarm and third alarm is at least one of a portion color-coded with special color or colors.

\* \* \* \* \*